United States Patent [19]

Finley et al.

[11] Patent Number: 4,482,506

[45] Date of Patent: Nov. 13, 1984

[54] PROCESS FOR THE MANUFACTURE OF ALKYL DIARYL PHOSPHATE ESTERS

[75] Inventors: Joseph H. Finley, Metuchen; Hsiang P. Liao, Princeton, both of N.J.

[73] Assignee: FMC Corporation, Philadelphia, Pa.

[21] Appl. No.: 432,472

[22] Filed: Oct. 4, 1982

[51] Int. Cl.³ .............................................. C07F 9/09
[52] U.S. Cl. ...................................... 260/982; 260/965
[58] Field of Search .................................. 260/982, 965

[56] References Cited

U.S. PATENT DOCUMENTS

| | | | |
|---|---|---|---|
| T903,016 | 10/1972 | Cleveland | 260/982 |
| 2,504,121 | 4/1950 | Gamrath | 260/461 |
| 3,056,823 | 10/1962 | Hechenbleikner et al. | 260/461 |
| 3,184,496 | 5/1965 | Baranauckas et al. | 260/461 |
| 3,363,033 | 1/1968 | Witt | 260/982 |
| 3,422,453 | 1/1969 | Frank | 260/982 |
| 3,576,923 | 4/1971 | Randell et al. | 260/966 |

FOREIGN PATENT DOCUMENTS 0025720  3/1981  European Pat. Off. .......... 260/98 L

OTHER PUBLICATIONS

W. H. C. Rueggeberg et al., in J. Am. Chem. Soc. 70, 1802, (1948).
Abstract of Polish Pat. No. 78616 from C.A.

*Primary Examiner*—Anton H. Sutto
*Attorney, Agent, or Firm*—Robert D. Jackson; Eugene G. Horsky

[57] ABSTRACT

Mixed phosphoric acid ester compositions containing less than 4 weight percent of a triaryl phosphate, from about 10 to about 20 weight percent of an aryl dialkyl phosphate and from about 65 to about 80 weight percent of an alkyl diaryl phosphate are prepared by heating a monohydric alcohol or alkoxy alcohol with a triaryl phosphate, such as triphenyl phosphate, in the presence of a catalytic amount of an alkali metal phenoxide, for example, potassium phenoxide. The mixed phosphoric acid ester composition may be separated from by-products of the reaction by distillation.

6 Claims, No Drawings

PROCESS FOR THE MANUFACTURE OF ALKYL DIARYL PHOSPHATE ESTERS

This invention relates to a process of producing esters of orthophosphoric acid. More particularly, it pertains to an improved process of manufacturing alkyl diaryl phosphate esters by the transesterification of a triaryl phosphate with an aliphatic alcohol.

Alkyl diaryl phosphate esters constitute a known class of valuable and useful chemical entities. For instance, these esters, which are generally nearly colorless liquids, have exceptional utility as flexibilizing plasticizers for polyvinyl chloride compositions, imparting to those compositions the combination of properties of flexibility at freezing temperatures, low volatility losses of plasticizer at higher temperature and low flammability. Because of their very low pour points and very high autogenous ignition temperatures and their compatibility with paraffinic hydrocarbon oils, these monoalkyl diaryl phosphates may be used alone or in combination with paraffinic hydrocarbon oils to prepare hydraulic and torque converter fluids of highly desirable characteristics. Moreover, such esters have a wide variety of other uses, such as lubricants for mechanisms from delicate clock works to extreme pressure bearing surface, film-forming addition agents in hydrocarbon oils for use in extreme pressure lubricants and as a liquid medium for filters for air conditioning systems.

Various methods are known for producing alkyl aryl phosphates. One common procedure consists of reacting 2 moles of a phenolic compound with 1 mole of phosphorus oxychloride, removing the HCl formed under vacuum followed by reacting the diphenyl phosphoryl chloride with 1 mole of an aliphatic alcohol. There is a problem, however, in controlling the reaction to avoid forming excessive quantities of triaryl derivatives. In another known procedure, the starting material is a triaryl phosphate, which is made to undergo alkaline hydrolysis to cleave off one aryl group, the mixture subjected to steam distillation and then replacing the eliminated aryl with an alkyl group. The drawback here is that it involves several steps which greatly increase operating costs. A further method described is that of reacting in excess of 1 mole of an aliphatic alcohol with 1 mole of phosphorus oxychloride, removing the HCl formed under vacuum, purifying the monoalkyl phosphoryl dichloride by distillation and subsequently reacting at a relatively high temperature the purified acid chloride with 2 moles of phenol or similar hydroxy aryl compound. However, not all aliphatic alcohols are suited to this reaction. Also, many of the alkyl phosphoryl dichlorides are thermally unstable and undergo varying decomposition at the temperatures they are reacted with the hydroxyaryl compounds. A still further method of realizing alkyl diaryl phosphate is that described in U.S. Pat. No. 2,504,121. According to this reference, one molecular proportion of a $C_6$ to $C_{13}$ primary alkyl alcohol or beta-alkoxyethyl alcohol, wherein the alkyl substituent consists of an alkyl radical of at least 4 and not more than 18 carbon atoms, is reacted with one molecular proportion of phosphorus oxychloride, while continuously removing the HCl formed under vacuum, thereby forming in essentially quantitative yields, requiring no further purification, the monoalkyl phosphoryl dichloride. The latter is then added under controlled conditions to substantially two molecular proportions of sodium arylate in an aqueous solution. The resultant monalkyl diaryl phosphate thus formed in high yields is separated from the aqueous reaction mass, washed with water and dilute alkali and dehydrated under vacuum. The problem with this method is the large quantities of sodium salts which are difficult to remove and dispose of when operating on a commercial scale. In addition, the side reaction of alkyl phosphoryl dichloride with an alcohol results in substantial quantities of alkyl halide being formed as a by-product. And of course, this process, like most of the others aforesaid, share in the common feature of evolving highly poisonous and corrosive HCl gas.

Another familiar synthetic tool in the field of organophosphorus chemistry is transesterification. This reaction, sometimes referred to as ester interchange or alcoholysis, has been extensively documented in connection with the preparation of organic phosphites. For instance, U.S. Pat. Nos. 3,056,823 and 3,184,496 disclose the synthesis of trialiphatic phosphite esters by the transesterification of triaryl phosphites, such as triphenyl phosphite with an aliphatic alcohol in the presence of a basic catalyst. By contrast, very little prior art seems to exist dealing with the application of transesterification to the production of phosphates. Admitted, there is considerable documentation describing the preparation of "mixed esters" from an organophoshpate and stoichiometric quantities of an alkoxide as depicted in the following scheme:

$(RO)_3PO + R_1ONa \rightarrow (RO)_2POR_1 + RONa$     Eq. 1

However, the reaction aforesaid is not true transesterification in which the ester interchange takes place in the presence of a catalytic amount of alkoxide. An early study on the transesterification of organic phosphates was reported by W. H. C. Rueggeberg et al in J. Am. Chem. Soc. 70, 1802 (1948). According to these authors, it was found that alkali metal alkoxides, specifically sodium butoxide, behave as catalysts in the transesterification of triethyl phosphate butanol. Much later, in a recently issued (1975) Polish Pat. No. 78,616, there is described the transesterification of a triaryl phospate with an aliphatic alcohol containing 6 to 12 carbon atoms in its molecule in the presence of 0.25-12 parts of sodium or potassium by weight at a temperature of 20° C.-200° C. for 1-10 hours, wherein the weight ratio of triaryl phosphate to alcohol may vary between 100:40 and 100:200. One technical advantage claimed in the Polish patent is that this process yields a final product of greater purity. The sole example of this patent, however, gives an impure residue that is dark yellow to brown in color which decomposes when attempts are made to purify it by vacuum distillation.

An improvement in the preparation of monoalkyl diaryl phosphates via base catalyzed transesterification is set forth in EPC Publication No. 25720 of Mar. 25, 1981. This document discloses a method of making such mixed phosphoric acid ester compositions by reacting in an anhydrous system and in the presence of a catalytic amount of sodium, a phosphoric acid ester:

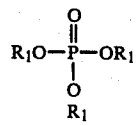

wherein $R_1$ may be the same or a different aromatic radical selected from the group consisting of phenyl and substituted phenyl radicals, with an alipatic alcohol having the formula:

$$R_2CH_2-CH_2OH$$

wherein $R_2$ is the same or a different aliphatic radical selected from the group consisting of alkyl and alkoxy radicals. This application teaches that the mixed phosphoric acid ester composition so obtained may be separated as a colorless liquid from impurities present in the transesterification mixture by vacuum distillation. The EPC publication emphasizes that maintaining anhydrous conditions throughout the reaction is critical in effecting the transesterification reaction by the process therein described. That publication teaches that, "...As many of the alcohols employed, and particularly the lower molecular weight alcohols are hydroscopic, precautions must be taken that all reactants are thoroughly dry. The presence of moisture has a pronounced effect on the transesterification of esters of phosphoric acid and modifies the composition of the reaction product to an extent that does not occur in the alcoholysis of esters derived from organic acids."

A further improvement on preparing alkyl diaryl phosphates by base catalyzed transesterification is disclosed in our copending application filed on even date herewith.

In accordance with that application, a mixed phosphoric acid ester composition is manufactured by heating about 2.06 moles of an alcohol characterized by a boiling point above about 170° C. and having the formula:

$$R_2CH_2CH_2OH$$

wherein $R_2$ is the same or a different aliphatic radical selected from the group consisting of alkyl and alkoxy alkyl radicals with about 0.036 mole of an aqueous sodium hydroxide solution under vacuum to distill off the water present in the mixture and form sodium alkoxide in situ. The reaction mixture is then heated to about 100° C. under a blanket of nitrogen and about 1 mole of a triaryl phosphate having the formula:

$$(R_1O)_3P''O$$

wherein $R_1$ is the same or a different aromatic radical selected from the group consisting of phenyl and substituted phenyl radicals is added with agitation. The agitation is continued for about 1 hour while maintaining the reaction mixture at a temperature of about 100° C. under a nitrogen atmosphere. The by-product phenol and any residual aliphatic alcohols are then volatilized from the reaction mixture by applying vacuum and increasing the temperature from about 100° C. to about 140° C. The reaction mixture is next filtered to remove insoluble salts and finally distilled under vacuum and at a temperature below the decomposition temperature of the mixed phosphoric acid ester composition formed to recover the desired product.

A further improvement in the preparation of monoalkyl diaryl phosphate by the base catalyzed transesterification of a triaryl phosphate with an alcohol has now been discovered and the provision of said improvement constitutes the principal object and purpose of the invention.

In accordance with the invention, there is provided a process for the manufacture of a substantially monoalkyl diaryl phospate having the formula:

$$R_1O-\overset{\overset{O}{\|}}{\underset{OR_1}{P}}-OCH_2CH_2R_2$$

wherein $R_1$ is the same or a different aromatic radical selected from the group consisting of phenyl and substituted phenyl radicals and $R_2$ is the same or a different aliphatic radical selected from the group consisting of alkyl and alkoxy radicals, which comprises:
(a) heating about 2.0 moles of an alcohol characterized by a boiling point above about 170° C. and having the formula:

$$R_2CH_2CH_2OH$$

wherein $R_2$ is the same or a different aliphatic radical selected from the group consisting of alkyl and alkoxy radicals with a catalytic amount of a phenoxide to form an alkoxide of said alcohol and phenol in accordance with the following equilibria:

$$\phi OM + R_2CH_2CH_2OH \rightleftharpoons \phi OH + R_2CH_2CH_2OM$$

wherein M is an alkali metal.
(b) adding to the equilibria reaction mixture of step (a) about 1.0 mole of a triaryl phosphate of the formula:

$$(R_1O)_3P=O$$

under nitrogen atmosphere and maintaining the temperature at about 100° C. with agitation for about an hour;
(c) heating the reaction mixture from step (b) at 100° C. to 140° C. under vacuum to remove aromatic and aliphatic alcohols from the reaction mixture;
(d) filtering the reaction mixture from the preceding step, and
(e) distilling the filtrate in a wiped film still under vacuum and at a temperature below the decomposition temperature of said mixed phosphoric acid ester composition to obtain the desired product.

The triaryl phosphate that may be employed as a starting material in the process of this invention may be triphenyl phosphate or methyl substituted phenyl phosphate such as cresyl phosphate, xylenyl phosphate or the synthetic isopropylphenyl/phenyl phosphates referred to above and described in U.S. Pat. No. 3,576,923. Particularly preferred is triphenyl phosphate because the phenol which is recovered as a by-product from this reaction may be isolated from the reaction mixture and recycled to manufacture additional triphenyl phosphate.

The alcohols and alkoxy alcohols that are useful in the process of the present invention are those having a boiling point above about 170° C. such as butoxyethanol, n-decanol, and isodecanol. Particularly preferred is a mixture of isomeric $C_{10}$ alcohols that are substantially free of substitution on the alpha- and beta-carbon atoms that are a by-product of the petroleum industry. This alcohol may be purchased from the Exxon Chemical Company, Houston, Tex. having the following technical specifications:

| | |
|---|---|
| Acidity, as acetic acid (wt. percent) max | 0.001 |
| Appearance | Clear and Free of Suspended Matter |
| Carbonyl Number (mg KOH/g) max | 0.20 |
| Color (Pt-Co) max | 10.00 |
| Distillation (°C.) | |
| Initial min | 215.00 |
| Dry Point max | 223.00 |
| Purity (wt. percent) min | 99.00 |
| Specific Gravity (20/20° C.) max | 0.840 |
| Specific Gravity (20/20° C.) min | 0.835 |
| Water (wt. percent) max | 0.1 |

The phenoxide catalyst is desirably an alkali metal phenoxide such as sodium or potassium phenoxide. Typically, alkali metal phenoxides can be prepared by reacting the metal with a phenol or by adding a solution of the alkali metal hydroxide to the phenol followed by removal of the water. A technique has been discovered, however, whereby the phenoxide catalyst can be satisfactorily introduced into the transesterification reaction mixture without having to use alkali metals or remove water. Generally, these are undesirable factors in large-scale chemical processes. Alkali metals, for example, sodium, are highly flammable which can even explode in the presence of moisture; water removal steps are to be avoided because of evaporative energy costs and high capital investment for the requisite plan equipment.

The production of phenoxide transesterification catalysts by the process of the invention obviates the disadvantages aforesaid by forming the phenoxide from an alkali metal carbonate and a phenolic compound in accordance with the following scheme:

$$R_1OH + M_2CO_3 \rightarrow R_1OM + MHCO_3 \qquad \text{Eq. 2}$$

wherein $R_1$ is a phenyl as previously defined and M is an alkali metal.

It will be observed that the alkali metal phenoxide is generated under anhydrous conditions. That is, water is not added to the reactants nor is any formed, the sole reaction products being the phenoxide and alkali bicarbonate. This method of producing phenoxide catalyst not only eliminates the water-evaporative step but utilizes a much safer and easier to handle source of the alkali metal, that is, alkali metal carbonate, rather than flammable elemental alkali metals or corrosive alkali metal hydroxides.

So far as can be ascertained, any alkali metal carbonate is suitable for producing alkali metal phenoxides by the process of the invention. Econimic considerations generally limit the practical choices to sodium or potassium carbonate. Of these two, potassium carbonate performed the best in that it gave a higher percent transesterification conversion. Thus, during the period of reaction using potassium carbonate, a conversion of 96.0% was attained; 47% was a typical percent conversion using sodium carbonate. It is thought that better results were obtained with the potassium carbonate because of its higher solubility in the reaction mixture.

In a preferred method of carrying out the process of the invention, approximately equimolar quantities of anyhdrous potassium carbonate, preferably finely ground, and phenol are added to an aliphatic alcohol of the formula $R_2CH_2CH_2OH$ defined elsewhere herein and the mixture heated under an inert atmosphere until the reaction is complete, typically about one hour at about 130° C. A triaryl phosphate of the formula $(R_1O)_3PO$ is then added and transesterification carried out at a temperature of about 100° C. for about one hour after which the temperature is increased to about 100° C. to about 140° C. and aromatic and aliphatic alcohols removed in vacuo. The residual reaction mixture is freed of solids and then subjected to distillation in a wiped film still to give the monoalkyl diaryl phosphate as heretofore defined, the $C_{10}$ alcohols being preferred as the source of the alkyl group.

So far as can be determined, the mechanism of transesterification in the presence of phenoxide involves the following two steps: (1) an equilibrium reaction of alkali metal phenoxide with the aliphatic alcohol to form the alkali metal salt thereof and a phenol compound, and (2) a rapid reaction between the triaryl phosphate and alkali metal alkoxide. These reactions can be represented by the following equations in which the alcohol is decanol; the triaryl is triphenyl phosphate and the alkali metal is potassium.

$$C_6H_5OK + C_{10}H_{21}OH \rightleftharpoons C_{10}H_{21}OK + C_6H_5OH \qquad \text{Eq. 3}$$

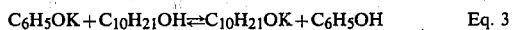

$$(C_6H_5O)PO + C_{10}H_{21}ONa \rightarrow (C_6H_5O)_2P(O)OC_{10}H_{21} + C_6H_5OK \qquad \text{Eq. 4}$$

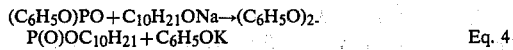

The equilibrium described in Equation 3 ordinarily lies far to the left. However, it is displaced to the right by the rapid reaction of alkoxide with triphenyl phosphate. With potassium carbonate/phenol in a dry (0.1% by weight $H_2O$) system, a 96% conversion to the monoalkyl diaryl phosphate composition was obtained.

Although its function in the transesterification is that of a catalyst, the alkoxide is eventually depleted due to the occurrence of side reactions. For instance, analytical investigations established that a white solid, which precipitated during the transesterification, was alkali metal diphenyl phosphate. It is formed along with a corresponding ether by-product under anhydrous conditions by the side reaction of alkoxide with alkyl diaryl phosphate as depicted below with sodium isodecylate and isodecyldiphenyl phosphate.

$$C_{10}H_{21}OP(OC_6H_5)_2 + 2C_{10}H_{21}ONa \longrightarrow$$

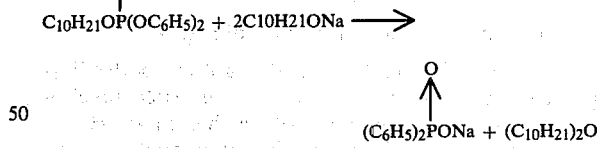

$$(C_6H_5)_2PONa + (C_{10}H_{21})_2O$$

Eq. 5

Where there is moisture present in the transesterification mixture, this can also lead to the formation of the alkali metal diaryl phosphate through hydrolysis of the triaryl phospate. In fact, the hydrolysis is rapid and exothermic. It can thus be seen that by-products are minimized by conducting the transesterification in the anhydrous state and that this condition is preferably established by generating the phenoxide in situ by reacting phenol with potassium carbonate as previously described. By operating in essentially the absence of moisture while maintaining a catalyst concentration of about 0.02 to 0.04, preferably about 0.04 mole/mole of triphenyl phosphate, the transesterification process of the invention provides optimum results.

Where the alcohol is an unsubstituted alkanol, that is $R_2$ is alkyl, the weight ratio of the phosphate esters in the final product is: less that about 6% triarylphosphate; about 65% to about 80% of an alkyl diaryl phosphate and about 15% to about 20% of an aryl dialkyl phosphate. Where the alcohol is an alkoxy alkanol, that is R is alkoxy, there is an increase in the yield of the aryl dialkyl phosphate component. Apparently, the alkoxy alkanols are more reactive than the unsubstituted alkanols, a structural feature which tends to promote the formation of the disubstituted product. Using a catalyst concentration of about 2% (mole % based on the phenol reactant) the weight of phosphate ester typically runs as follows: less than about 9% triarylphosphate; about 65% of an alkoxyalkyl diarlyl and about 25 to about 30% of an aryl di(alkoxyalkyl) phosphate. Use of higher concentrations of catalyst seems to favor increased yields of the aryl di (alkoxyalkyl) phosphate.

The invention is illustrated but not to be taken as limited by the following examples.

EXAMPLE 1

Potassium Phenoxide Catalyst from Phenol and $K_2CO_3$

To 100 gm (0.632 moles) of isodecanol, containing less than 0.1% water (by Karl-Fisher titration) was added 3.32 gm (0.024 mole) of potassium carbonate and 2.44 gm (0.026 mole) of phenol. The mixture was heated under nitrogen with stirring at 130° C. for one hour. Triphenyl phosphate (100 gm, 0.306 mole) was added and the course of conversion versus time data at 130° C. are as follows:

| Time, hours | % Conversion |
|---|---|
| 0.58 | 82.0 |
| 1.58 | 94.9 |
| 2.25 | 95.9 |
| 3.33 | 96.0 |

These results indicate that potassium phenoxide is an effective catalyst for transesterification of triphenyl phosphate with isodecanol. The weight ratio of phosphate esters is: 4.0% triphenylphosphate; 21.7 diisodecylphosphate and 74.3% isodecyldiphenylphosphate.

EXAMPLE 2

Sodium Phenoxide from Phenol and $Na_2CO_3$

To 100 gm (0.63 mole) of isodecanol was added 2.44 gm (0.026 mole) of phenol and 2.78 gm (0.026 mole) of sodium carbonate. The mixture was heated at 160° C. for one hour after which a significant amount of undissolved material remained in suspension. Triphenyl phosphate (100 gm, 0.31 mole) was then added and the reaction mixture was maintained at 160° C. Gas chromatographic results are summarized below:

| Reaction Time, hours | % Conversion |
|---|---|
| 1.0 | 41 |
| 3.8 | 47 |

The lower conversion, compared to Example 1, may be attributed to the lower solubility (vs. $K_2CO_3$) of sodium carbonate in isodecanol. Nevertheless, the sodium phenoxide, produced by reaction between dissolved $Na_2CO_3$ and phenol, resulted in 47% conversion of triphenyl phosphate.

EXAMPLE 3

Sodium Phenoxide from Phenol and NaOH

Sodium phenoxide was prepared by combining 18.8 gm (0.2 mole) of phenol and 8.0 gm (0.2 mole) of solid sodium hydroxide in 60 ml of water. The mixture was stirred for 0.5 hours at room temperature. Most of the water was removed under reducted pressure in a rotary evaporator, resulting in 25.3 gm of partially hydrated product.

To a one liter 3-necked flask, equipped with an air-driven stirrer, nitrogen inlet tube, thermometer, Dean Stark trap and reflux condenser was added 300 gm (1.9 mole) of isodecanol and 5.3 gm of sodium phenoxide, prepared as described above. The mixture was heated at reflux (215° C.); water (1.5 ml) was collected in the Dean Stark trap. The mixture (under nitrogen) was cooled to 100° C. and 300 gm (0.92 mole) of triphenyl phosphate was added. The mixture was maintained at 100°. Conversion versus time data are as follows:

| Time, hours | % Conversion |
|---|---|
| 0.37 | 71.2 |
| 1.0 | 91.9 |
| 2.0 | 93.8 |
| 3.0 | 95.0 |

Phenol, ethers and unchanged isodecanol were removed by vacuum distillation (pot temperature 90° C.-160° C.; head temperatures 70° C.-75° C.; pressure 0.2-0.3 torr). The crude product was filtered through a Buchner funnel equipped with a fine porosity fritted glass disc. The filtrate contained 328.5 gm of material, which corresponds to a 91.5% yield as isodecyl diphenyl phosphate. The weight ratio of the phosphate esters is: 5.7% triphenylphosphate; 14.8% diisodecylphenylphosphate and 79.5% diphenylisodecylphosphate.

EXAMPLE 4

Transesterification of Triphenyl Phosphate with 2-Butoxyethanol in the Presence of Sodium Phenoxide A mixture of 460 gm (3.8 moles) of 2-butoxyethanol, 600 gm (1.84 moles) of triphenyl phosphate (TPP) and 1.9 mole % (based on TPP) of sodium phenoxide was heated under a nitrogen atmosphere at 130° C. following the procedures of the previous examples. A second run was carried out using the same procedure but with different amounts of catalyst and different reaction times. The results of the two runs were as follows:

| | | | Product Distribution (Wt. %) | | |
|---|---|---|---|---|---|
| | Sodium Phenoxide | | Dibutoxy-ethyl | Butoxy-ethyl | |
| Run # | Gm | Mole % on $C_6H_2O_2$ | Time Hrs. | Phenyl Phosphate | Diphenyl Phosphate | TPP |
| 1 | 8.8 | 1.9 | 5 | 27.1 | 64.2 | 8.6 |
| 2 | 13.2 | 3.0 | 2 | 39.2 | 59.1 | 1.6 |

What is claimed is:

1. A process for the manufacture of a substantially monoalkyl diaryl phosphate having the formula;

$$R_1O-\overset{\overset{O}{\|}}{\underset{OR_1}{P}}-OCH_2CH_2R_2$$

wherein $R_1$ is the same or a different aromatic radical selected from the group consisting of phenyl and substituted phenyl radicals and $R_2$ is the same or a different aliphatic radical selected from the group consisting of alkyl and alkoxy radicals, which comprises:

(a) heating about 2.0 moles of an alcohol characterized by a boiling point above about 170° C. and having the formula:

$$R_2CH_2CH_2OH$$

wherein $R_2$ is the same or a different aliphatic radical selected from the group consisting of alkyl and alkoxy radicals with a catalytic amount of a phenoxide to form an alkoxide of sid alcohol and phenol in accordance with the following equilibria:

$$\phi OM + R_2CH_2CH_2OH \rightleftharpoons \phi OH + R_2CH_2CH_2OM$$

wherein M is an alkali metal, the said phenoxide being an alkali metal phenoxide formed by the reaction of an alkali metal carbonate selected from the class consisting of sodium carbonate and potassium carbonate with phenol;

(b) adding to the equilibria reaction mixture of step (a) about 1.0 mole of a triaryl phosphate of the formula:

$$(R_1O)_3P=O$$

under a nitrogen atmosphere and maintaining the temperature at about 100° C. with agitation for about an hour;

(c) heating the reaction mixture from step (b) at 100° C. to 140° C. under vacuum to remove aromatic and aliphatic alcohols from the reaction mixture;

(d) filtering the reaction mixture from the preceding step, and (e) distilling the filtrate in a wiped film still under vacuum and at a temperature below the decomposition temperature of said mixed phosphoric acid ester composition to obtain the desired product.

2. The process of claim 1 wherein the phenoxide is potassium phenoxide formed by the reaction of potassium carbonate and phenol.

3. The process of claim 1 wherein the alcohol is n-decanol.

4. The process of claim 1 wherein the alcohol is iso-decanol.

5. The process of claim 1 wherein the alcohol is butoxyethanol.

6. The process of claim 1 wherein the triaryl phosphate is triphenyl phosphate.

* * * * *